United States Patent [19]

Sullivan

[11] 4,030,341

[45] June 21, 1977

[54] FLUID APPLICATION DEVICE

[75] Inventor: Kevin J. Sullivan, Raleigh, N.C.

[73] Assignee: Corning Glass Works, Corning, N.Y.

[22] Filed: July 24, 1975

[21] Appl. No.: 598,590

[52] U.S. Cl. .......................................... 73/61.1 C
[51] Int. Cl.² ........................................ G01N 1/00
[58] Field of Search .......... 118/401, 100, 506, 413; 23/259; 401/261, 265, 266; 427/2; 73/61.1, 61.1 C

[56] References Cited

UNITED STATES PATENTS

| | | | |
|---|---|---|---|
| 1,635,624 | 7/1927 | Imset | 401/266 |
| 1,934,796 | 11/1933 | Friederich | 118/401 |
| 3,358,496 | 12/1967 | Farmer | 118/401 X |
| 3,446,649 | 5/1969 | Degenhardt et al. | 118/401 X |
| 3,842,660 | 10/1974 | Van Buskirk | 73/61.1 C |

FOREIGN PATENTS OR APPLICATIONS 245,600   4/1912   Germany ........................... 401/265

*Primary Examiner*—Morris Kaplan
*Attorney, Agent, or Firm*—Walter S. Zebrowski; Clarence R. Patty, Jr.

[57] ABSTRACT

A fluid application device suitable for applying small quantities of blood to a microscope slide is described. The device has a housing within which a longitudinal aperture is formed. At one end of the aperture a transverse groove is formed which intersects the aperture. Small quantities of blood from a capillary tube may be introduced into the longitudinal aperture and permitted to spread through the transverse groove so that a relatively thin and uniform layer of blood is deposited on a microscope slide by drawing the device across a microscope slide.

4 Claims, 8 Drawing Figures

FLUID APPLICATION DEVICE

BACKGROUND OF THE INVENTION

The present invention relates to a device for applying small quantities of fluid to a surface such as the surface of a microscope slide. Heretofore, microscope slide preparation by the spinning technique required at least 250μL of blood to assure full coverage of the slide surface with a blood film or layer. This amount of blood is readily available if a venipuncture is performed on a patient. However, in many cases, particularly pediatrics, venipuncture is not desirable, and small volumes, typically 100μL maximum, of blood are drawn from a superficial skin puncture of the fingertip, heel, or earlobe. With such small quantities of blood it has heretofore been difficult to obtain a uniform layer of blood of sufficient thickness to permit a good blood slide for microscopic examination to be formed by the spinning process. Blood slides may be formed by applying a quantity of blood to the surface of a microscope slide and thereafter spinning it in a slide centrifuge such as that described in U.S. patent application Ser. No. 363,433 filed May 24, 1973, now U.S. Pat. No. 3,906,890, by L. G. Amos et al. and assigned to a common assignee with the present application.

Summary of the Invention

The objects of the present invention are to provide a device for applying a fluid to a surface, such as a microscope slide surface, which permits the formation of an acceptable spun film on a microscope slide with the utilization of a very small quantity of fluid, and one which permits ease of construction and is economical.

Broadly, according to the present invention, a device for applying a fluid to a surface is provided which includes a housing having two broad opposing surfaces and a plurality of peripheral edge surfaces. A longitudinal aperture extending from one of such edge surfaces substantially parallel to the broad opposing surfaces is formed therein. Further, a groove is formed in an other of the edge surfaces of the housing transverse to the longitudinal aperture and intersecting the longitudinal aperture at one end thereof. The surface embodying the groove may be formed with a convex curvature. The groove may have various shapes including a flat groove as well as one arcuately shaped.

Additional objects, features, and advantages of the present invention will become apparent to those skilled in the art from the following detailed description and the attached drawing on which, by way of example, only the preferred embodiments of this invention are illustrated.

DETAILED DESCRIPTION

Figure 1:
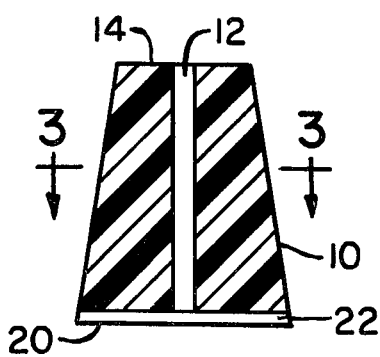
FIG. 1 is a front cross sectional view of the fluid applying device of the present invention.

It is to be noted that the Figures of the drawing are illustrative and symbolic of the invention, and there is no intention to indicate scale or relative proportion of the elements shown therein. Further, although the device of the present invention will be herein described in connection with applying blood to microscope slides, this is merely for convenience and brevity since the device is applicable to the application of any fluids to any surfaces.

Figure 2:
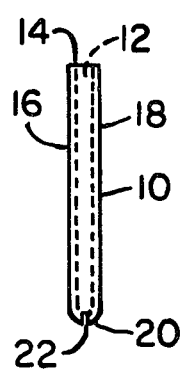
FIG. 2 is a side elevation of the device of FIG. 1.

Referring to FIGS. 1 and 2, there is shown the device of the present invention including housing 10 within which is formed a longitudinal aperture 12 that extends from one edge surface 14 parallel to the broad opposing surfaces 16 and 18 of housing 10. In another edge surface 20 of housing 10, a transverse groove 22 is formed intersecting aperture 12 at one end thereof. As will be understood, aperture 12 communicates with groove 22. Edge surface 20 within which groove 22 is formed may be flat or preferably convex as illustrated in FIG. 2.

Figure 3:
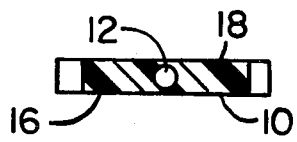
FIG. 3 is a cross sectional view taken along line 3—3 of FIG. 1.
Figure 4:
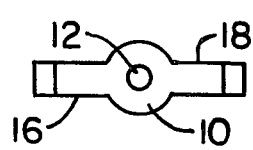
FIG. 4 is a top view of another embodiment of the device of the present invention.
Figure 5:
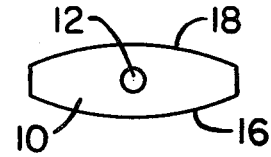
FIG. 5 is a top view of further embodiment of the device of the present invention.

FIGS. 2 and 3 illustrate a housing 10 wherein broad opposing surfaces 16 and 18 are substantially flat. The broad opposing surfaces may, however, be contoured as illustrated in FIG. 4 and 5. The specific configuration of surfaces 16 and 18 is not critical to this invention.

The material of housing 10 may be any suitable material compatible with the fluid employed such as, for example, glass, plastics, or the like.

Figure 6:
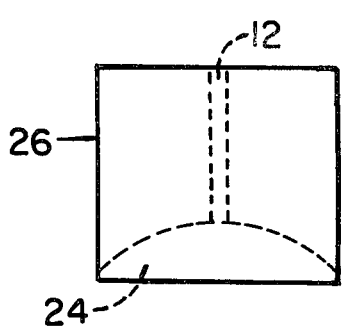
FIG. 6 is an elevational view of still another embodiment of the device of the present invention.

FIG. 6 illustrates another embodiment of the present invention wherein transverse groove 24 is formed having an arcuate shape as distinguished from the flat shape of groove 22. The shape of the transverse groove may be any shape so long as it communicates with longitudinal aperture 12 and permits the distribution of the fluid along the edge within which the transverse groove is formed. As is seen, groove 24 intersects and communicates with longitudinal aperture 12 at one end thereof within housing 26.

Figure 7:
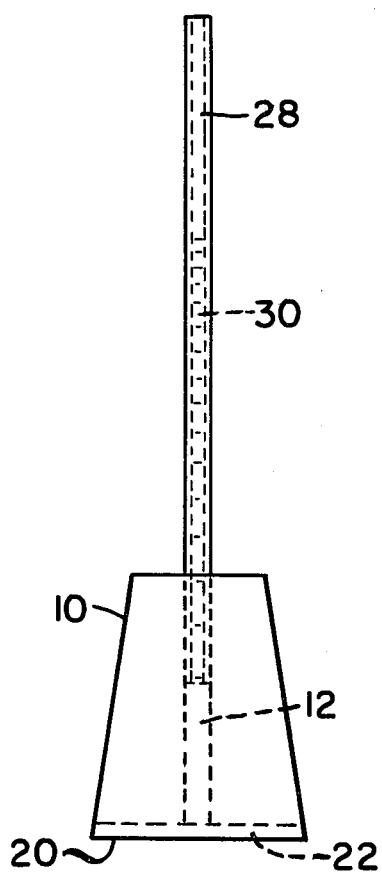
FIG. 7 is a front elevation of the device of FIG. 1 with a capillary tube in place.

The operation of the fluid applying device is as follows. Referring to FIG. 7, a sample of blood of approximately 25μL is drawn into a capillary tube 28 from a superficial skin puncture on the fingertip, heel, earlobe, or similar position of a body by means well known in the art. The capillary tube may be chemically treated, if desired, to prevent the blood from clotting. Capillary tube 28 containing blood 30 is then inserted into one end of longitudinal aperture 12 in housing 10. The blood then flows from the capillary tube to longitudinal aperture 12 and transverse groove 22 by capillary action and gravity to completely fill the transverse groove which is open across edge 20 of the device.

Figure 8:
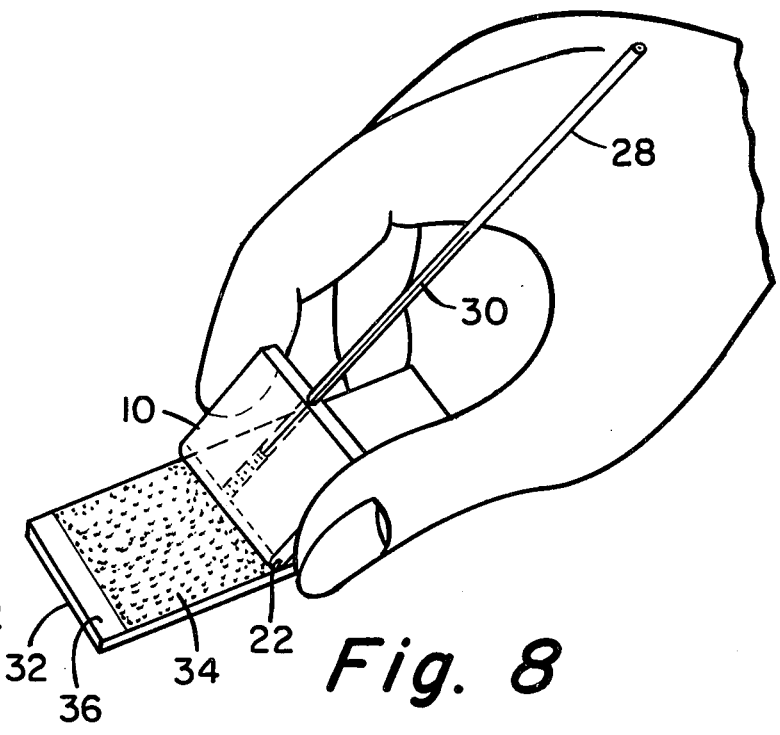
FIG. 8 is an oblique view of the device of the present invention used in applying a quantity of blood to a microscope slide.

Referring now to FIG. 8, the device is then placed with the transverse groove adjacent the surface of a glass microscope slide 32. Housing 10 of the device is then drawn along the length of the slide with transverse groove 22 adjacent the microscope slide surface producing a full wet film 34 of blood over most or all of the microscope slide surface 36 as illustrated in FIG. 5. For best results, microscope slide with wet blood film 34 thereon is immediately spun on a blood slide centrifuge of the type described in the heretofore noted Amos et al. patent application. Such procedure produces a high quality microscope slide having a uniform monolayer of blood cells which can thereafter be stained and examined in a manner well known in the art.

Another significant advantage of the fluid applying device of the present invention is that it can be inexpensively produced from glass or plastic and can be provided in conjunction with a capillary tube as an inexpensive disposable unit.

Although the present invention has been described with respect to specific details of certain embodiments thereof, it is not intended that such details be limitations upon the scope of the invention except insofar as set forth in the following claims.

I claim:

1. A device for applying a fluid to a surface comprising a housing having two broad opposing surfaces and a plurality of peripheral edge surfaces, one of said peripheral edge surfaces forming at least a part of the fluid applying face of said device, said applying face having a convex curvature, means embodied within said housing defining a longitudinal aperture adapted to receive a discrete capillary tube, said aperture extending from one of said edge surfaces substantially parallel to said broad opposing surfaces, means embodied within said housing defining a groove formed substantially entirely in said applying face of said device to a depth sufficient to permit said groove to communicate with said longitudinal aperture, said groove having a width of a dimension so as to retain any fluid disposed therein by surface tension until said fluid contacts said surface, said groove being tansverse to said longitudinal aperture and intersecting said longitudinal aperture at one end thereof, said groove forming a part of said applying face of said device, and a discrete capillary tube disposed within said longitudinal aperture.

2. the device of claim 1 wherein said groove is arcuately shaped.

3. The device of claim 1 wherein said broad opposing surfaces are flat.

4. The device of claim 1 wherein said broad opposing surfaces are contoured.

* * * * *